United States Patent [19]
Wong et al.

[11] Patent Number: 6,146,848
[45] Date of Patent: Nov. 14, 2000

[54] BACTERIAL EXPRESSION SYSTEM

[75] Inventors: Wan Keung Wong, Kowloon; Kat Hon Lam, Quarry Bay, both of The Hong Kong Special Administrative Region of the People's Republic of China

[73] Assignee: The Hong Kong University of Science & Technology, Kowloon, The Hong Kong Special Administrative Region of the People's Republic of China

[21] Appl. No.: 09/121,286

[22] Filed: Jul. 23, 1998

[51] Int. Cl.$^7$ ..................................... C12P 21/06
[52] U.S. Cl. ............... 435/69.1; 435/252.3; 435/252.31; 435/252.33; 435/320.1; 435/471; 536/24.1
[58] Field of Search ................ 536/24.1; 435/320.1, 435/252.3, 252.31, 252.33, 471, 69.1

[56] References Cited

U.S. PATENT DOCUMENTS

| 4,868,111 | 9/1989 | Bujard et al. | 435/68 |
| 4,935,370 | 6/1990 | Franke | 435/252.33 |
| 5,021,340 | 6/1991 | Toma et al. | 435/69.1 |
| 5,223,407 | 6/1993 | Wong et al. | 435/69.1 |

*Primary Examiner*—Remy Yucel
*Attorney, Agent, or Firm*—Baker Botts L.L.P.

[57] ABSTRACT

The present invention provides endonuclease-protected vegI promoters, constructs comprising same, bacteria transformed with same, expression products of said constructs produced by bacteria transformed with same, and methods of manufacturing said expression products using said transformed bacteria. Also provided are *E. coli* transformed with constructs having the vegI promoter, expression products of same and methods of manufacture of said expression products using said transformed *E. coli*.

26 Claims, 6 Drawing Sheets

BACTERIAL EXPRESSION SYSTEM

FIELD OF THE INVENTION

The present invention concerns a bacterial expression system, particularly for the expression of heterologous proteins, for use with gram-positive and gram-negative bacteria, particularly *Bacillus subtilis* and *E. coli*, the expression system comprising novel genetic constructs. Also provided is a novel promoter element for use in same.

BACKGROUND OF THE INVENTION

Various systems are available for expressing proteins in bacteria, and heterologous proteins are typically produced at high levels using *E. coli* as a host. However, *E. coli* is not always the most desirable host bacterium—in certain circumstances it is particularly advantageous to use *Bacillus subtilis*. The advantages of *B. subtilis* as an expression host include its non-pathogenicity, absence of significant codon bias (Brown, T. A., 1991, Genomes and Genes, In: T. A. Brown (Ed.), Molecular Biology Labfax, BIOS Scientific Publisher Ltd., Oxford, pp. 235–254), the presence of secretory mechanisms, its extensively studied genetics, and the facility of large-scale manipulation using standard protocols (Simonen, M. and Palva, I., 1993, Microbiological Reviews, 57: 109–137).

To date, protein expression using *B. subtilis* has been unsuccessful due to low product expression levels. This has resulted from the lack of efficient regulatory elements, both for transcriptional and post-transcriptional control of expression. One major problem encountered in *B. subtilis* is that at the onset of the stationary (S) growth phase it expresses large quantities of proteases which are detrimental to the integrity of the heterologous protein which is being expressed and therefore product expression during S-phase is unacceptably low. Efforts have been made to address this (Wong, S. L., 1995, Current Opinion in Biotechnology, 6: 517–522). This problem has been overcome in the past by the use of protease-deficient and endonuclease-defective strains. However, although able to express desired proteins at improved levels during S-phase, they suffer from the problem of typically being slow-growing strains and introducing additional expense and difficulties into the manufacturing process.

It has previously been suggested (Lam, K. H. E., Chow, K. C. and Wong, W. K., Abstract T3.36, Asia Pacific Society of Bioscientists, Second International Symposium and Workshop, Jul. 8–11 1996) to express proteins in *B. subtilis* during the vegetative growth phase (VGP) using an expression/secretion cassette comprising the *B. subtilis* veg promoter, the *E. coli* lac operator, the Staphylococcal protein A leader sequence for secretion, a multiple cloning region, translational stop codons and the efficient *B. subtilis* gnt transcriptional terminator. The cassette may be cloned into a modified *B. subtilis/E. coli* shuttle vector pRB373M2 to form an expression/secretion vector named the veg vector. The endoglucanase (Eng) gene and the human epidermal growth hormone gene (hEGF) were stated as having been cloned into the veg vector.

The present inventors have now succeeded in making a novel expression cassette, particularly for use in *B. subtilis* and *E. coli*, which allows very high expression levels of heterologous proteins to be achieved in *B. subtilis*.

Previously, the use of the vegI promoter alone in *B. subtilis* has not been described—the use of the veg (comprising the vegI and vegII promoters) (see for example U.S. Pat. No. 4,783,405; U.S. Pat. No. 4,710,464; U.S. Pat. No. 4,559,300) and vegII (see for example Le Grice, F. J., 1990, Methods Enzymol., 185: 201–214) promoters in heterologous protein expression has been described. As a result of the isolation and purification of an unexpected vegI mutant occurring at very low levels (a total of five *B. subtilis* transformants were found to harbour plasmid DNA containing the mutant vegI promoter in a transformation in which about 300 μg of DNA was used), it has now been found that a *B. subtilis* endonuclease activity appears to act upon the vegI promoter, causing digestion and subsequent exonuclease digestion of the promoter. The present inventors have succeeded in isolating the putative vegI promoter *B. subtilis* endonuclease restriction site, allowing the modification of the palindromic restriction site to protect against *B. subtilis* endonuclease activity and allow the use of the modified vegI promoter. One particular modified vegI promoter is described below but other modifications may be readily made to the vegI promoter to protect against the endonuclease activity whilst still retaining the promoter functionality. This allows the use of the vegI promoter alone with *B. subtilis*, not previously suggested by the prior art. The identification of the palindromic endonuclease restriction site is particularly surprising since it is an octameric sequence, whereas most endonuclease restriction sites are hexamers.

According to the present invention there is provided an endonuclease-protected vegI promoter, and particularly a *B. subtilis* endonuclease-protected vegI promoter.

The present inventors have found that the octameric sequence of SEQ ID NO: 20, which forms part of the −10 region of the vegI promoter, is a *B. subtilis* endonuclease restriction site, meaning that constructs containing the vegI promoter undergo endonuclease (and subsequently, exonuclease) digestion when transformed into *B. subtilis*. This in turn results in the construct failing to express any coding sequences it contains.

The identification of the endonuclease restriction site has allowed the development of endonuclease-protected vegI promoters which are protected against endonuclease restriction digestion, yet which still retain their promoter functionality. Specifically, the fifth residue of SEQ ID NO: 20 may be substituted from A to G to give the endonuclease-protected sequence of SEQ ID NO: 21. The endonuclease restriction site is typically found at nucleotides −15 to −8 of the vegI promoter relative to the transcription start nucleotide beginning at nucleotide +1 (nucleotide 51 of SEQ ID NOs: 12 and 13) (Le Grice, S. F. J. et al., 1986, Mol. Gen. Genet., 204: 229–236). An example of an endonuclease-protected vegI promoter is that of SEQ ID NO: 12. The sequence of a typical vegI promoter is that of SEQ ID NO: 13.

Alternatively endonuclease-protection may be achieved by other nucleotide substitutions to the octamer. The substitutions may be simply made and the efficacy of the substituted readily determined using the experimental procedures detailed below. Alternatively, nucleotides of the restriction site may be methylated using primers with specifically methylated nucleotides and the standard procedures of PCR and subcloning. Other substitutions will be readily apparent to one skilled in the art and may be readily made and the efficacy of modified promoters simply determined.

Also provided according to the present invention is a DNA construct for expressing a coding sequence in *B. subtilis*, comprising operatively linked in the 5' to 3' direction:

a) an endonuclease-protected vegI promoter;

b) a DNA coding sequence encoding an RNA encoding an expression product; and c) a 3' non-translated region.

It may additionally comprise between said endonuclease-protected vegI promoter and said DNA coding sequence a lac operator, ribosome binding site, and SPA leader sequence. Said 3' non-translated region may comprise a stop codon and the gnt transcriptional terminator.

Said DNA coding sequence may comprise the coding sequence for a heterologous protein, for example the *Cellulomonas fimi* cenA coding sequence or the human epidermal growth factor (hEGF) coding sequence. The successful results obtained (below) expressing both hEGF and endoglucanase (Eng), two very different heterologous proteins, shows that such a construct is capable of successfully expressing a wide range of proteins. Other heterologous proteins which may be expressed using the construct of the present invention include human interleukin 1 (Bellini, A. V. et al., 1991, J. Biotech. 18: 177–192) and the antidigoxin single-chain antibody (Wu, X. C. et al., 1993, Bio/Technology, 11: 71–76). Other proteins will be readily apparent to one skilled in the art.

Also provided according to the present invention is a DNA construct for expressing a coding sequence in *B. subtilis*, comprising operatively linked in the 5' to 3' direction:

a) an endonuclease-protected vegI promoter;

b) at least one cloning site into which may be inserted a DNA coding sequence encoding an RNA encoding an expression product; and c) a 3' non-translated region.

In such a construct, the cloning site may comprise a multiple cloning site. The construct may additionally comprise between said endonuclease-protected vegI promoter and said cloning site a lac operator, ribosome binding site, and SPA leader sequence. Said 3' non-translated region may comprise a stop codon and the gnt transcriptional terminator. An example of such a construct is that detailed in FIG. 1.

Also provided according to the present invention is a bacterium transformed with a DNA construct according to the present invention. Experiments (below) detail *B. subtilis* transformed with such a construct. Experiments have also shown that expression can be successfully achieved in *E. coli*. Successful expression my also be achieved in other bacteria, for example *Staphylococcus aureus*, the pRB373 shuttle vector (see below) having been derived from the *S. aureus* plasmid pUB110 (Gryczan, T. J. et al., 1978, J. bacterial., 134: 318–329).

Also provided according to the present invention is the expression product of a DNA construct according to the present invention made by a bacterium transformed with same. Such an expression product may be isolated and purified.

Also provided according to the present invention is a method of manufacture of an expression product of a gene, comprising the steps of:

a) transforming a bacterium with a DNA construct according to the present invention containing the coding sequence of said gene for said expression product;

b) culturing said bacterium to cause expression of said coding sequence; and c) isolating and purifying said expression product.

As detailed above, experiments have shown that *E. coli* transformed with a construct having an endonuclease-protected vegI promoter are capable of successfully expressing the coding sequence of the construct. It has now also been found that, surprisingly, *E. coli* transformed with a construct having an unmodified vegI promoter are also capable of expressing the coding sequence of the construct. Thus the present invention also provides an *E. coli* bacterium transformed with a DNA construct for expressing a coding sequence, said DNA construct comprising operatively linked in the 5' to 3' direction:

a) the vegI promoter;

b) a DNA coding sequence encoding an RNA encoding an expression product; and c) a 3' non-translated region.

Such a use of a vegI promoter has neither been suggested nor disclosed by the prior art.

Also provided according to the present invention is the expression product of a DNA construct made by an *E. coli* bacterium according to the present invention, transformed with said DNA construct.

Also provided according to the present invention is a method of manufacture of an expression product of a gene, comprising the steps of:

a) culturing a transformed *E. coli* according to the present invention, said *E. coli* having been transformed with a DNA construct containing the coding sequence of said gene for said expression product, said culturing causing expression of said coding sequence; and b) isolating and purifying said expression product.

Also provided according to the present invention is a vegI promoter having a guanine nucleotide substituted at position −11 relative to the transcriptional start nucleotide beginning at nucleotide +1.

The invention will be further apparent from the following description, with reference to the several figures of the accompanying drawings, which show, by way of example only, form of *B. subtillis* expression systems.

DETAILED DESCRIPTION OF THE INVENTION

Experimental

Materials and Methods

Bacterial strains, transformation, growth media and conditions *B. subtilis* strains DB104 (his, nprR2, nprE18, aprEΔ3), 1A751 (eglSΔ102, bglT/bglSΔEV, npr, apr, his) and 1A510 (arg[GH]15, leuB8, thrA, recA4, stp$^r$, r$^-$m$^-$), which were used as host strains for the expression of hEGF and *C. fimi* Eng, were obtained from the Bacillus Genetics Stock Centre at Ohio. *E. coli* strain JM101 (supE, thi, Δlac-proAB [F', tra36, proAB$^+$, lacI$^q$ZΔM15]), used as the intermediate host for recombinant DNA work, was described previously (Sambrook et al., 1989, Molecular Cloning: A Laboratory Manual. Cold Spring Harbor Laboratory Press, Cold Spring Harbor, N.Y.).

*B. subtilis* cells were grown at 37° C. in LB medium (Sambrook et al., 1989, supra), and transformants were grown in the same medium supplemented with 20 μg ml$^{-1}$ of kanamycin. *E. coli* transformants were grown at 30° C. in 2YT medium (Sambrook et al., 1989, supra) supplemented with 70 μg ml$^{-1}$ of ampicillin. For solid media, Bacto agar was added at a concentration of 1.5% (w/v). Carboxymethylcellulose (CMC) agar plates employed for detecting Eng activity were prepared as previously described (Gilkes, N. R. et al., 1984, J. Biol. Chem., 259: 10455–10459).

Transformation of *E. coli* and *B. subtilis* with recombinant plasmids was performed using the calcium chloride (Mandel, M. and Higa, A., 1970, J. Mol. Biol., 53: 159–162) and Spizizen's (Spizizen, J., 1958, Proc. Natl. Acad. Sci. U.S.A., 44: 1072–1078) methods, respectively.

DNA manipulations

Polymerase chain reaction (PCR) was performed according to a protocol previously described (Sambrook et al., 1989, supra). Site-specific mutagenesis was carried out by overlap extension using PCR (Ho, S. N. et al., 1989, Gene 77: 51–59). DNA fragments of interest were cloned into the replicative form of M13mp18 (Yanisch-Perron, C. et al., 1985, Gene, 33: 103–119) and sequence then determined by the dideoxy method (Sanger, F., 1981, Science, 214: 1205–1210) using a T7 sequencing kit (Pharmacia).

Assembly of the Veg cassette

Figure 1:
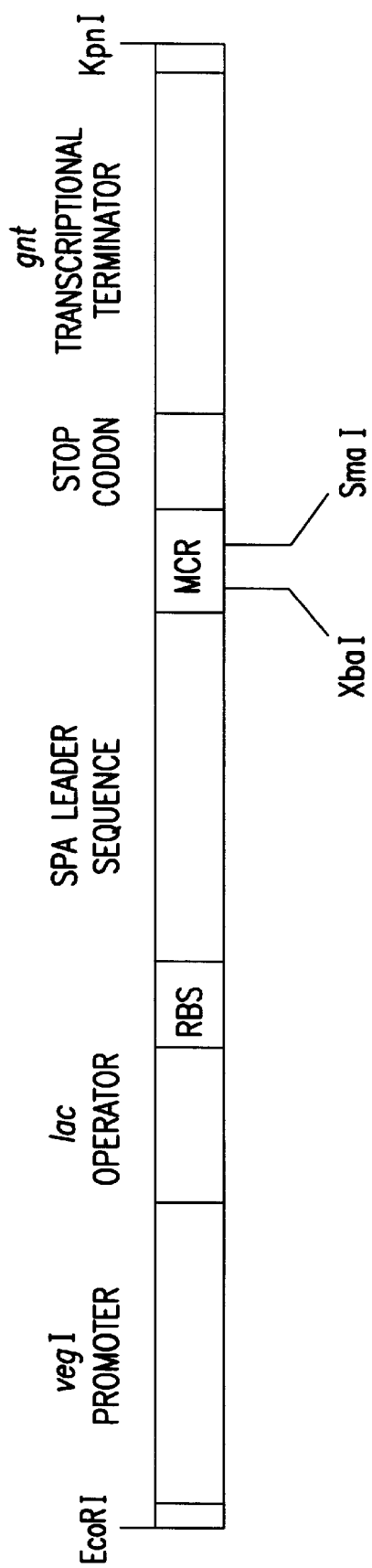
FIG. 1 shows the Veg cassette. (A) Schematic representation of the regulatory elements in the Veg cassette. The cassette is 356 bp in length. RBS, SPA and MCR stand for ribosome-binding site, Staphylococcal protein A and multiple-cloning region, respectively. The sequences of the wild-type (unprotected) vegI promoter, lac operator, RBS, SPA leader sequence, MCR, stop codon and gnt transcriptional terminator are given by SEQ ID NOs: 13–19 respectively. The sequence of the endonuclease-protected vegI promoter is given by SEQ ID NO: 12. The translational start codon TTG is residues 1–3 of SEQ ID NO: 16.

To assemble the 356 bp Veg cassette having the endonuclease-protected vegI promoter (FIG. 1), eight single-stranded oligonucleotides (A–H) having the sequences of SEQ ID NOs: 1–8 respectively were designed and synthesized. Oligos A, B, C and D consisted of sequences of the coding strand and were 70, 67, 67 and 70 nucleotides in length, respectively; oligos E, F, G and H contained sequences of the non-coding strand and were 68, 67, 67 and 20 nucleotides long, respectively. These two groups of oligos shared complementary overlapping sequences at their ends, all of which were 20 nucleotides in length. The eight oligos were annealed and the gaps were filled with the Klenow enzyme to get a double-stranded product. Subsequent to amplification by PCR using oligos A and H as the primers, the assembled DNA cassette, flanked by an EcoRI site and a KpnI site, was cloned into the M13mp18 vector and integrity confirmed by DNA sequencing. The Veg cassette consists the *B. subtilis* vegI promoter (which represents the RNA polymerase binding site I of the veg promoter complex) (Le Grice, S. F. J. et al., 1986, supra), the *E. coli* lac operator (Le Grice, S. F. J. et al., 1987, Gene 55: 95–103), the *B. subtilis* consensus ribosome-binding site (Mountain, A., 1989, Gene expression system for *Bacillus subtilis*. In: Harwood, C. R. (Ed.), Biotechnology Handbooks, vol. 2: Bacillus. Plenum Press, N.Y., pp. 73–114), the Staphylococcal protein A leader sequence (Fahnestock, S. R. and Fisher, K. E., 1986, J. Bacteriol., 165: 796–804), and the gnt transcriptional terminator (Fujita, Y. et al., 1986, J. Biol. Chem., 261: 3744–3753) were included in the cassette, together with the flanking EcoRI and KpnI sites, a multiple cloning region (MCR) containing restriction sites for XbaI and SmaI, and a sequence containing stop codons in all reading frames. Nucleotides 11–70 of oligo A (SEQ ID NO: 1) correspond to nucleotides 1–60 of the vegI promoter (SEQ ID NO: 12). Nucleotides 1–13 of oligo B (SEQ ID NO: 2) corresponds to nucleotides 4–16 of the RBS (SEQ ID NO: 15). Nucleotides 14–67 of oligo B (SEQ ID NO: 2) corresponds to nucleotides 1–54 of the SPA leader sequence (SEQ ID NO: 16). Nucleotides 1–57 of oligo C (SEQ ID NO: 3) corresponds to nucleotides 82–138 of the SPA leader sequence (SEQ ID NO: 16). Nucleotides 58–67 of oligo C (SEQ ID NO: 3) corresponds to nucleotides 1–10 of the MCR (SEQ ID NO: 17). Nucleotides 1–60 of oligo D (SEQ ID NO: 4) corresponds to nucleotides 11–70 of the gnt transcriptional terminator (SEQ ID NO: 19). Nucleotides 49–68 of oligo E (SEQ ID NO: 5) corresponds to the complementary strand to nucleotides 60–41 of the vegI promoter (SEQ ID NO: 12). Nucleotides 24≧48 of oligo E (SEQ ID NO: 5) corresponds to the complementary strand to nucleotides 25–1 of the lac operator (SEQ ID NO: 14). Nucleotides 8–23 of oligo E (SEQ ID NO: 5) corresponds to the complementary strand to nucleotides 16–1 of the RBS (SEQ ID NO: 15). Nucleotides 1–7 of oligo E (SEQ ID NO: 5) corresponds to the complementary strand to nucleotides 7–1 of the SPA leader sequence (SEQ ID NO: 16). Nucleotides 1–67 of oligo F (SEQ ID NO: 6) corresponds to the complementary strand to nucleotides 101–35 of the SPA leader sequence (SEQ ID NO: 16). Nucleotides 58–67 of oligo G (SEQ ID NO: 7) corresponds to the complementary strand to nucleotides 138–129 of the SPA leader sequence (SEQ ID NO: 16). Nucleotides 46–57 of oligo G (SEQ ID NO: 7) corresponds to the complementary strand to nucleotides 12–1 of the MCR (SEQ ID NO: 17). Nucleotides 31–45 of oligo G (SEQ ID NO: 7) corresponds to the complementary strand to nucleotides 15–1 of the stop codon (SEQ ID NO: 18). Nucleotides 1–30 of oligo G (SEQ ID NO: 7) corresponds to the complementary strand to nucleotides 30–1 of the gnt transcriptional terminator (SEQ ID NO: 19). Nucleotides 11–20 of oligo H (SEQ ID NO: 8) corresponds to the complementary strand to nucleotides 70–61 of the gnt transcriptional terminator (SEQ ID NO: 19).

Construction of vectors

Figure 2:
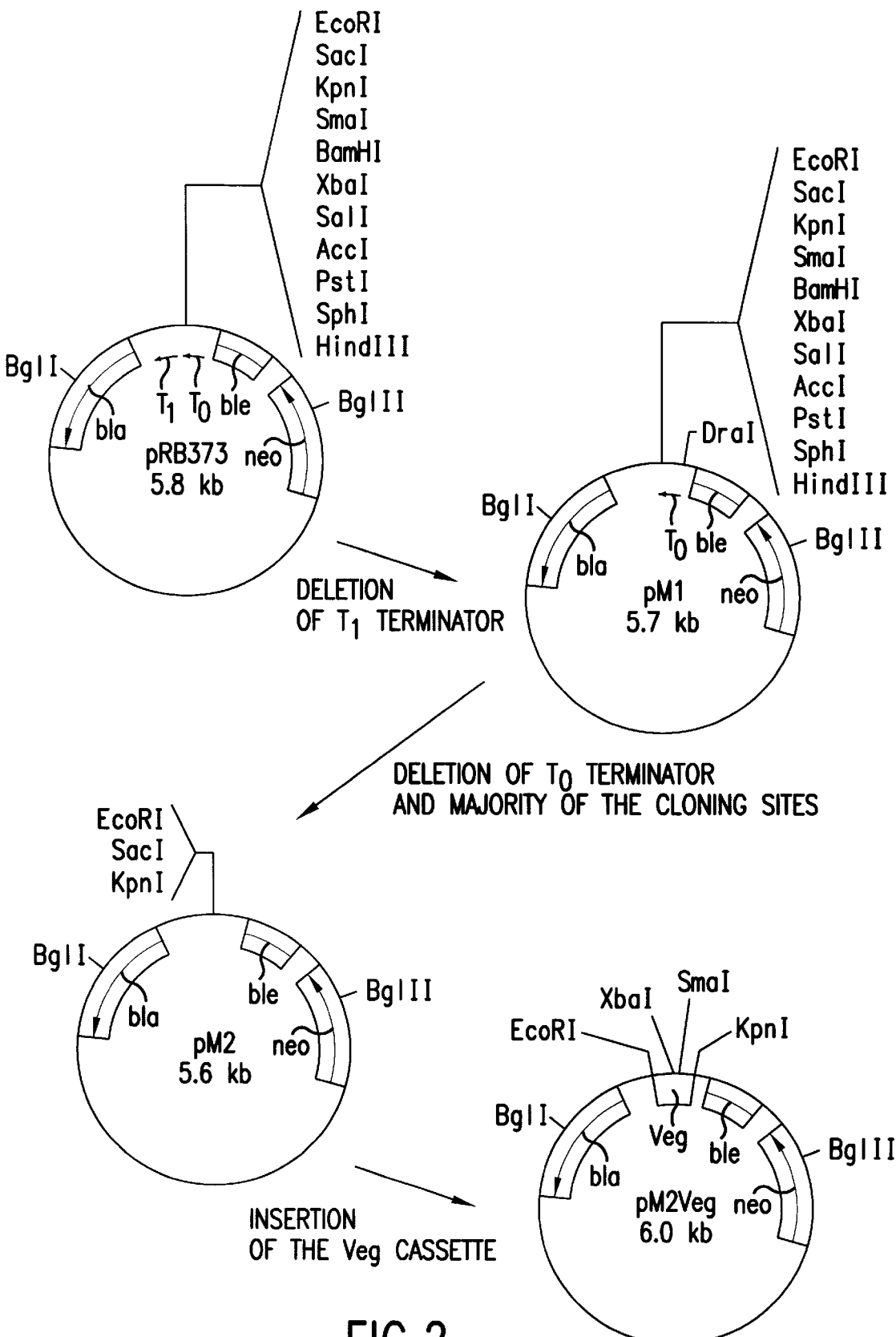
FIG. 2 shows the construction of the pM2Veg vector. The arrows within plasmids denote the directions of transcription. pM1 is made from pRB373 by the deletion of the $T_1$ terminator. pM2 is made from pM1 by the deletion of the $T_0$ terminator and the majority of the cloning sites. pM2Veg is made from pM2 by the insertion of the Veg cassette. Bla, ampicillin resistance determinant; ble, bleomycin resistance determinant; neo, neomycin resistance determinant.

To engineer an appropriate vector (see FIG. 2) to harbor the Veg cassette, the stable B. subtilis/E. coli shuttle vector, pRB373 (Brückner, R., 1992, Gene. 122: 187–192), was employed and modified. With two subcloning steps, most of the multiple-cloning sites (MCS) from the SmaI site to the HindIII site, and the $T_1$ and $T_0$ transcriptional terminators for foreign gene expression, were deleted from the vector to form first an intermediate construct, pM1, and subsequently, the target construct pM2. $T_0$ delete the $T_1$ terminator, the smaller BglI-EcoRI fragment containing the terminator and the 3' portion of the bla gene was replaced by a BglI-EcoRI segment obtained from pBR322 containing a functionally equivalent terminal sequence of the bla gene except for the absence of the $T_1$ terminator. The construct, designated pM1, was modified by replacing a 1.1 kb fragment, from the SmaI site in the MCS to the unique BglII site in pM1, with a 0.98 kb DraI-BglII segment derived also from pM1. The replacement deleted most of the restriction sites of the MCS except for the small segment from the EcoRI site to the KpnI site, and also deleted the $T_0$ transcriptional terminator. The resulting construct was designated pM2. The Veg cassette was then removed from the M13 construct as an EcoRI-KpnI fragment and cloned in the pM2 plasmid to form the B. subtilis expression/secretion vector, pMV2Veg.

Engineering of the recombinant construct expressing hEGF

The hEGF gene was available from a previously-engineered M13 construct (Wong, W. K. R. and Sutherland, M. L., 1993, U.S. Pat. No. 5,223,407) in which the gene was fused to the E. Coli ompA leader sequence. The full-length hEGF gene together with the 3' portion of the ompA leader sequence were subcloned by blunt-end ligation as a NruI-PstI fragment from the M13 construct into the XbaI site of the Veg cassette contained in M13mp18, to form a M13Veg-EGF construct. To eliminate the ompA sequence and to fuse the HEGF gene precisely to the Staphylococcal protein A (SPA) leader sequence in the Veg cassette, the M13Veg-EGF construct was subjected to site-specific mutagenesis mediated by overlap extension using PCR (Ho et al., 1989, supra). Four PCR primers were employed in the operation, which included: the M13 reverse primer (#1233, New England Biolabs) (primer a, SEQ ID NO: 9); a 60-mer oligo containing the 3' terminal 30 nucleotides of the non-coding sequence of the SPA leader sequence and the 5' terminal 30 nucleotides of the non-coding sequence of the hEGF gene (primer b, SEQ ID NO: 10); the 5' terminal 30 nucleotides of the coding sequence of the hEGF gene, (primer c, SEQ ID NO: 11); and oligo H (primer d; SEQ ID NO: 8) were employed. In the first round of PCR amplification of the M13Veg-EGF construct, two double-stranded products, designated AB and CD, were generated using primer pairs a plus b and c plus d, respectively. Product AB was 290 bp long and contained sequence of M13mp18 covering the EcoRI site and its flanking regions, the Veg cassette DNA to the end of the SPA leader sequence, and the first ten codons of the hEGF gene. Product CD was 279 bp long and contained the entire sequence of the hEGF gene, the 3' portion of the Veg-cassette and a KpnI site. Products AB and CD were denatured and annealed at an overlapping region containing the first ten codons of the hEGF gene, and the recombinant molecule was PCR amplified using primers a and d to yield a final product containing the hEGF gene precisely fused to the SPA leader sequence. Integrity of the Veg-EGF fusion product was confirmed by DNA sequencing in M13mp18 and it was then subcloned as an EcoRI-KpnI fragment into vector pM2 to form the expression construct, pM2VegEGF.

Cloning and expression of the cenA gene of C. fimi in pM2Veg

To examine the application of the pM2Veg vector, the cenA gene of C. fimi, which encodes an endoglucanase (Eng) product that can be easily detected (Wong, W. K. R. et al., 1988, Bio/Technology, 6: 713–719), was employed as the reporter gene. Since previous studies showed that the N-terminal domain of Eng was not essential for enzymatic activity (Wong, W. K. R. et al., 1986, Gene, 44: 315–324; Warren, R. A. J. et al., 1986, Proteins, 1: 335–341), a partial cenA gene, starting at the 46th codon (where a BamHI site is located) was employed. A 1.2 kb BamHI-SacI fragment containing the truncated cenA sequence was isolated from plasmid pEC2.1 (Wong, W. K. R. et al., 1986, supra) and subcloned into the XbaI site of the pM2Veg vector that had been made flush with the Klenow enzyme. The resulting construct, designated pM2VegCenA, in which the cenA gene was fused in-frame with the SPA leader sequence, was transformed into three B. subtilis strains: 1A751, 1A510 and DB104.

The cultures (see FIG. 3) were grown on a LB agar plate supplemented with 0.1% CMC and 20 $\mu$g ml$^{-1}$ kanamycin at 37° C. overnight. The presence of Eng activity was indicated by the formation of a clear zone on the agar plate after staining with 0.2% Congo red and destaining with 5% NaCl.

Figure 3:
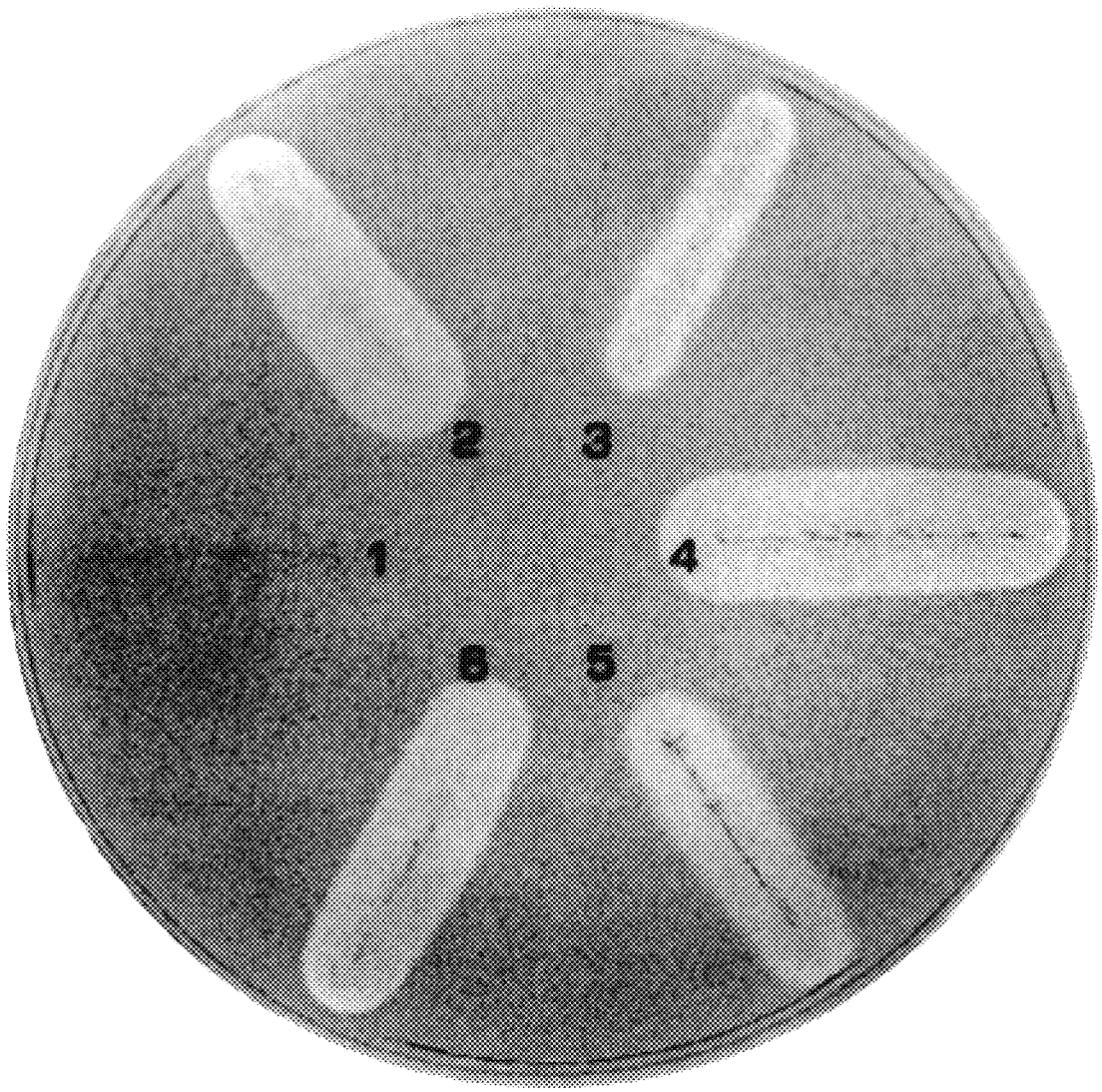
FIG. 3 shows expression of Eng activities by various *B. sublilis* transformants detected by the CMC plate assay. Transformants 1A751 [pM2VegCenA], DB104 [pM2VegCenA] and 1A510 [pM2VegCenA] are represented by the numbers 2, 4, and 6, respectively, whereas transformants 1A751 [pM2Veg], DB104 [pM2Veg] and 1A510 [pM2Veg] are given numbers 1, 3, and 5, respectively. Transformants 1–6 are plated out clockwise from a 9 o'clock position (transformant 1)—transformant 2–6 are at 11 o'clock, 1 o'clock, 3 o'clock, 5 o'clock and 7 o'clock positions respectively.

When the expression of Eng by the three transformants was compared with that of controls containing the pM2Veg vector using the CMC plate assay (Wong, W. K. R. et al., 1988, supra), the test cultures clearly produced bigger halos than did the control group (FIG. 3). The contrast is particularly obvious when transformants 1A751 [pM2VegCenA] and 1A751 [pM2Veg] are compared (FIG. 3). The negative result from transformant 1A751 [pM2Veg] indicated that strain 1A751 was an inefficient secretor of endogenous Eng, and therefore, transformant 1A751 [pM2VegCenA] was employed for quantitative studies of secretory production of the recombinant Eng encoded by cenA.

Figure 4:
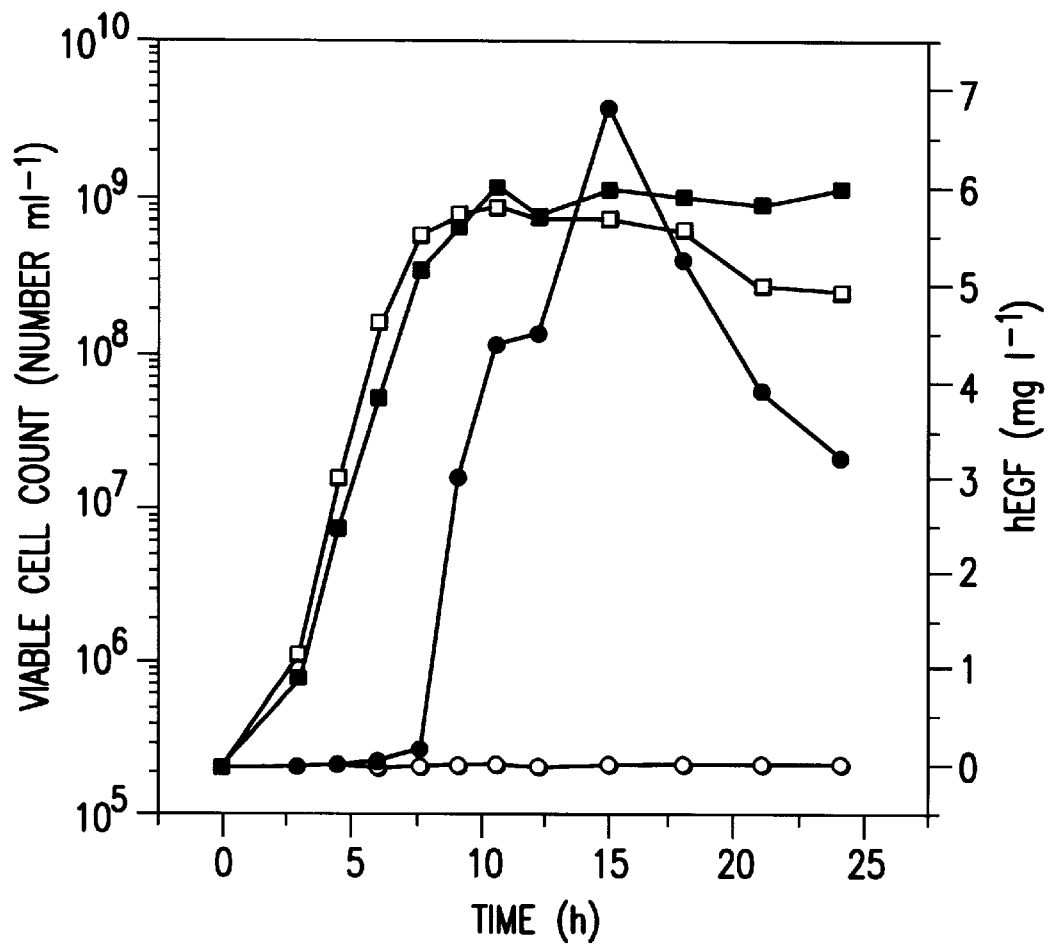
FIG. 4 shows extracellular production of Eng by *B. subtilis* 1A751 transformants. X-axis shows time in hours; left-hand Y-axis shows viable cell count (number ml$^{-1}$); right-hand Y-axis shows endoglucanase activity (U ml$^{-1}$). Activities of Eng produced by the 1A751 [pM2VegCenA] (—●—) and 1A751 [pM2Veg] (—○—) cultures are shown. Viable cell counts of 1A751 [pM2VegCenA] (—■—) and 1A751 [pM2Veg] (—□—) transformants were enumerated by plating the dilutions on LB agar medium supplemented with kanamycin.

The ability of transformant 1A751 [pM2VegCenA] to produce extracellular Eng was shown by the high levels of the enzyme attained in a time-course study (see "Assays for Eng", below) using transformant 1A751 [pM2Veg] as the negative control (FIG. 4). In accordance with the results of the CMC plate assay (FIG. 3), no extracellular Eng could be detected from transformant 1A751 [pM2Veg] throughout the time-course study (FIG. 4). However, a strikingly different result was observed with the 1A751 [pM2VegCenA] culture. After a short period of active growth of 1A751 [pM2VegCenA], during which recombinant Eng was presumably expressed and prepared for secretion, Eng activity was detectable in the culture medium. The level of secreted activity increased sharply until 30 hours, to a peak of 8.3 U ml$^{-1}$, even though the stationary growth phase had long been reached at the 15 hours timepoint (FIG. 4). The results showed that the viable cells in the stationary phase still actively secreted Eng, suggesting that the vegI promoter might function even beyond the log phase. This is supported by the fact that the veg gene is actively transcribed in both growing and sporulating cells (Haldenwang, W. G. et al., 1981, Cell 23: 615–624). The high stability of Eng, the active function of the vegI promoter, and the high densities of viable cells including those which might still secrete Eng for a few generations and could not be registered by the viable cell counts (Lam, T. L. et al., 1997, supra), appear to all contribute to the high levels of Eng detected in the stationary phase. Despite the likelihood that an even better yield may be attainable with growth beyond the 30 hour timepoint, the value seen is already more than 4 times that of the best value ever obtained from the expression of the same gene using other systems (Skipper, N. et al., 1985, Science, 230: 958–961; Paradis, F. W. et al., 1987, Gene, 61: 199–206.; Guo, Z. et al., 1988, FEMS Microbiol. Lett., 49: 279–283; Wong, W. K. R. et al., 1988, supra). The expression/secretion vector pMV2Veg has been found to be stably maintained in *B. subtilis* as reflected by growth and expression in media with or without selective pressure. In addition, secretory expression of Eng by the vector did not seem to impose any unfavorable effect on plasmid stability and cell viability (FIG. 4). When the efficiency of secretion of recombinant Eng from transformant 1A751 [pM2VegCenA] was studied, it was found that over 99% of the Eng activity encoded by cenA was secreted to the culture medium, after taking the minute level of intracellular endogenous Eng activity produced by the 1A751 host into consideration (Table 1, below).

The high level of Eng expressed by the pM2VegCenA construct in *B. subtilis* described above, is unlikely to be the best attainable yield, as is suggested by the low cell densities attained in this study (FIG. 4). With the use of richer media for cell growth, and probably also the inclusion of the lacI$^q$ gene (Bagdasarian, M. M. et al., 1983, Gene 26: 273–282) in the construct for synchronized and inducible production of Eng at a high cell density, an even higher level of Eng should be obtainable. A refined Veg-cassette-based *B. subtilis* system may be used not only to produce high levels of recombinant Eng, but may also be employed to attain efficient expression of other heterologous cellulases. The high efficiencies are essential to the formulation of a cost-effective enzymatic approach for cellulose saccharification.

Assays for Eng

Eng activity was quantified by the colorimetric assay using CMC as substrate (Gilkes et al., 1984, supra). One unit of Eng activity is defined as the amount of enzyme capable of releasing one $\mu$mol of glucose equivalents per minute at 37° C. Detection of Eng activity on CMC plates was performed as described previously (Gilkes et al., 1984, supra). Cell lysates for the determination of intracellular Eng activities were prepared using a French press according to the procedure described previously (Lam, T. L. et al., 1997, Enzyme Microb. Technol., 20: 482–488).

Assays for hEGF

Mouse BALB/C 3T3 (ATCC CCL163) cells employed for determining mitogenic activity of hEGF were grown in Dulbecco's modified Eagle medium (Gibco) supplemented with 4.5 g glucose l$^{-1}$, 10% fetal bovine serum (Gibco), 50 U penicillin ml$^{-1}$, and 50 $\mu$g streptomycin ml$^{-1}$. When the culture attained confluent growth, aliquots of 1×10$^4$ cells in 200 $\mu$l medium were inoculated into a 96-well tissue culture plate and grown for 10 days at 37° C. without medium change to induce quiescence.

Mitogenic activities of hEGF in culture supernatant samples were quantified by determining $^3$H-thymidine incorporation in quiescent 3T3 cells using the method previously described (Klagsbrun, M. et al., 1977, Exp. Cell Res., 105: 99–108; Shing, Y. et al., 1987, Methods Enzymol., 146: 42–48). Samples were first passed through 0.2 $\mu$m filters (Millipore), diluted to appropriate concentrations with 0.15 M NaCl. Up to 50 $\mu$l of a mixture containing a diluted sample and methyl-$^3$H-thymidine at a final concentration of 4 $\mu$Ci ml$^{-1}$ (5 Ci mmol$^{-1}$; Amersham) were added to the cells in each well and incubation proceeded for about 40 hours at 37° C. Measurement of the incorporation of $^3$H-thymidine into DNA was performed as follows. The medium was removed and the wells were washed once with 0.15 M NaCl. The solution was discarded and the wells were soaked with methanol twice, each time for a period of 5 minutes. Afterwards, the wells were washed four times with water then soaked twice with ice-cold 5% trichloroacetic acid (TCA), each time for a period of 10 minutes at 4° C., and subsequently washed four times with water. The TCA-precipitated materials were dissolved in 200 $\mu$l of 0.3 N NaOH and counted in 2 ml of scintillation fluid (Ready Solve, Beckman) using a scintillation counter (LKB-Wallac 1209 RackBeta, Pharmacia). The quantity of expressed hEGF was estimated by referring to a standard curve prepared using a commercial recombinant hEGF product (Promega).

Western blot analysis for hEGF

Aliquots of the DB104 [pM2VegEGF] and DB104 [pM2Veg] culture supernatants (1.2 ml each) collected at different timepoints were concentrated by first precipitation with ice-cold TCA at a final concentration of 5%. Subsequent to centrifugation, each precipitate was washed once with cold acetone and then resuspended in 80 $\mu$l sample buffer (2% SDS, 2% 2-mercaptoethanol, 10% glycerol, 62.5 mM Tris-HCl, pH 6.8). Forty microliters of the sample were used for analysis. The proteins that had been resolved on a 15% tricine-SDS-polyacrylamide gel (Schagger, H. and Von Jagow, G., 1987, Anal. Biochem., 166: 368–379) were transferred onto a polyvinylidene difluoride membrane (#162-0184, Bio-Rad) and reacted with a commercial anti-hEGF antibody (#pc08, Calbiochem) according to a protocol described previously (Ausubel, F. M. et al., 1993, Chapter 10: analysis of proteins. Current protocols in molecular biology. Vol. 2. John Wiley & Sons, Inc.).

Results and Discussion

Design of the Veg expression/secretion cassette

Since high levels of extracellular proteases are produced by *B. subtilis* at the onset of the stationary growth phase (Sloma, A. el al., 1990, Cloning and deletion of the genes for three minor extracellular proteases of *Bacillus subtilis*. In: Zukowski, M. M., Ganesan, A. T. and Hoch, J. A. (Eds.), Genetics and Biotechnology of Bacilli, vol. 3. Academic Press, N.Y., pp. 295–302; Priest, F. G., 1989, Products and applications. In: Harwood, C. R. (Ed.), Biotechnology Handbooks, vol. 2: Bacillus. Plenum Press, N.Y., pp. 293–320), foreign proteins expressed as secretory products by this organism during this growth phase are prone to be easily degraded. Therefore, to circumvent these difficulties in expressing foreign proteins in *B. subtilis*, the system of the present invention performs efficient expression and secretion of heterologous products into the culture medium during the vegetative growth phase.

Cloning and expression of hEGF gene in pM2Veg

Figure 5:
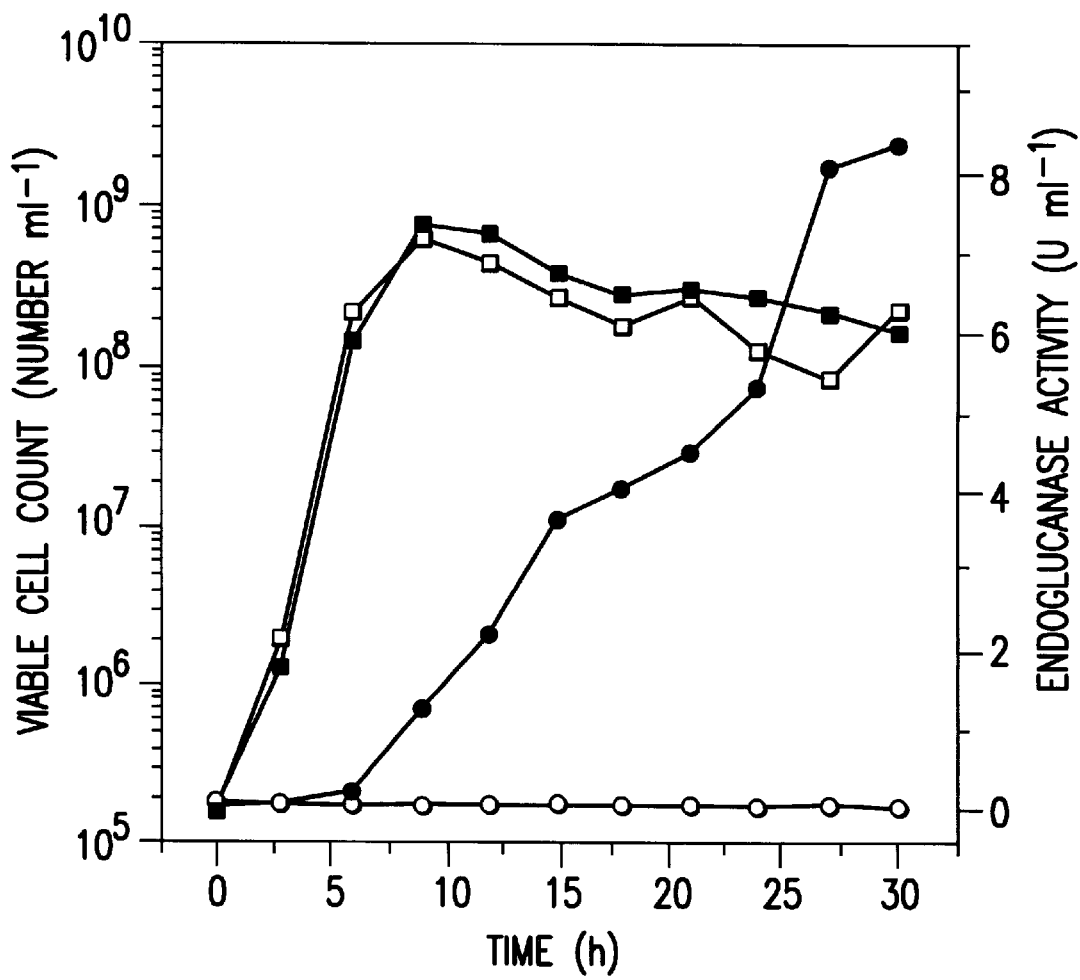
FIG. 5 shows extracellular production of hEGF by *B. subtilis* DB104 transformants. X-axis shows time in hours; left-hand Y-axis shows viable cell count (number ml$^{-1}$); right-hand Y-axis shows hEGF (mg l$^{-1}$). The amounts of hEGF produced by the DB104 [pM2VegEGF] (—●—) and DB104 [pM2Veg] (—○—) cultures are shown. Viable cell counts of DB104 [pM2VegEGF] (—■—) and DB104 [pM2Veg] (—□—) transformants were enumerated by plating the dilutions on LB agar medium supplemented with kanamycin.
Figure 6:
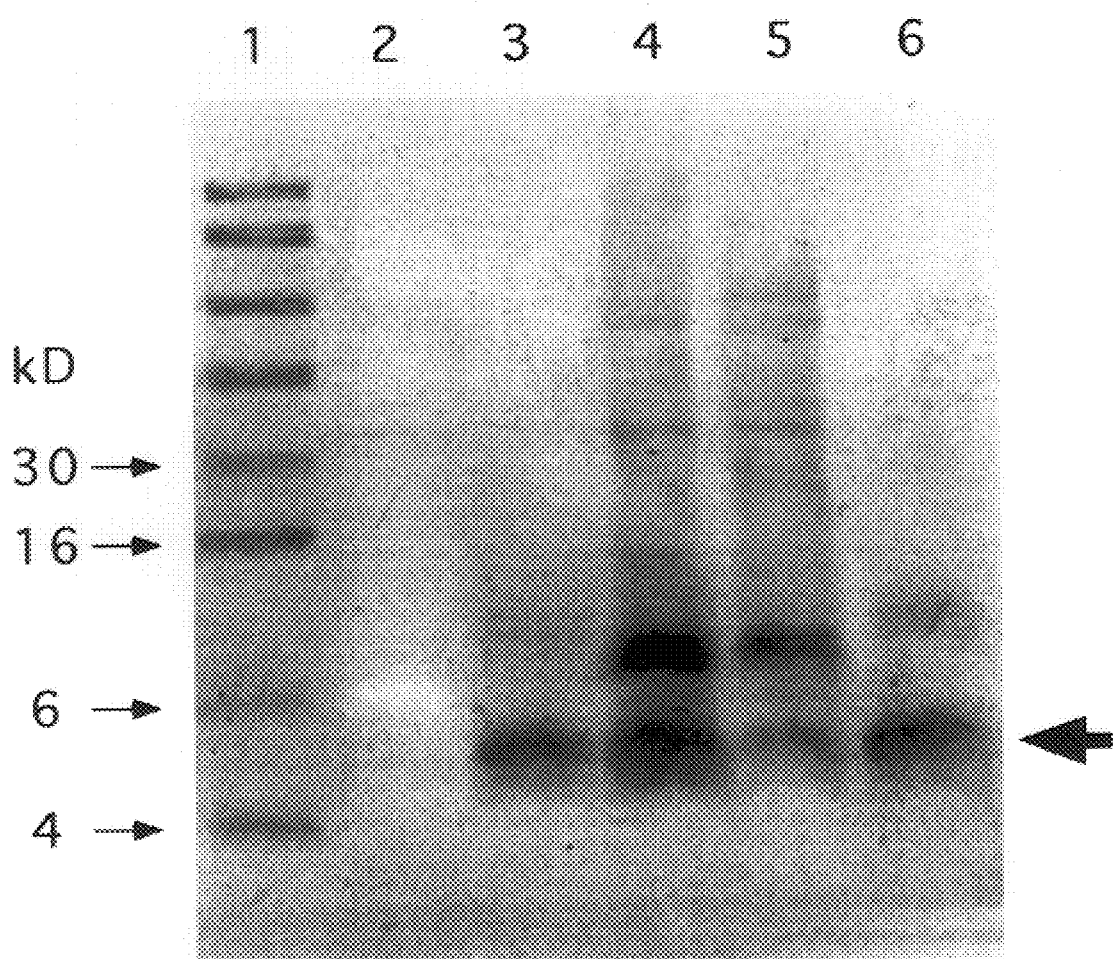
FIG. 6 shows Western blot analysis of the supernatant samples of *B. subtilis* DB104 cultures for the expression of hEGF. Culture supernatants were processed as described in the "Western blot analysis for hEGF" section below. Lanes: 1, molecular weight markers (#LC562, Novel Experimental Technology); 2, sample from a 15 hours old DB104 [pM2Veg] culture; 3 and 6,0.5 μg recombinant hEGF (Promega); 4, sample from a 15 hours old DB104 [pM2VegEGF] culture; 5, sample from a 24 hours old DB104 [pM2VegEGF] culture. The arrow indicates the position of the monomeric hEGF, kD, kilodaltons.

The versatility of the pM2Veg vector to express proteins widely different from the Eng product with respect to origin, chemical and physical properties, was studied using hEGF as a model. The recombinant construct formed between vector pM2Veg and the hEGF gene, designated pM2VegEGF (above), was transformed into the B. subtilis DB104 strain and expression of hEGF in the culture supernatant of the transformant was determined in a time-course study using a mitogenic assay (above). A DB104 [pM2VegEGF] culture grown in LB medium supplemented with kanamycin for 15 hours, 4 hours after the onset of the stationary phase, was found to produce a maximum level of about 7 mg $l^{-1}$ of secreted hEGF (FIG. 5). The decreased levels of hEGF detected at the later timepoints resulted likely from proteolytic activities. When the culture supernatant samples collected from different timepoints were analysed by Western blotting using a commercial anti-hEGF antibody (above; FIG. 6), the results revealed not only the integrity of the hEGF product in the samples, but also the difference in quantity of the products in the samples collected at different timepoints as expected from the time-course study (FIG. 5). In addition to the monomeric hEGF, the samples contained also a large proportion of the peptide existing presumably as a dimeric product (FIG. 6), which appeared to be more resistant than its monomeric counterpart to proteolysis. Despite the fact that hEGF has been expressed in a variety of recombinant systems, this is the first report of successful expression of hEGF as an extracellular product by B. subtilis. Even in the absence of any optimization, the level of hEGF detected is quite comparable to those obtained using other systems (Clements, J. M. et al., 1991, Gene, 106: 267–272; Morioka-Fujimoto, K. et al., 1991, J. Biol. Chem., 266: 1728–1732).

The success in expressing both Eng and hEGF employing the novel pM2Veg vector shows that the vector may be employed to express a wide variety of heterologous proteins in B. subtilis.

TABLE 1

Eng activities detected from various *Bacillus subtilis* cultures

| | Activity (U ml$^{-1}$ of culture) | | % recombinant |
|---|---|---|---|
| Strain | Intracellular | Extracellular | Eng detected |
| 1A751 | 0.020 | N.D. | N.A. |
| 1A751 [pM2Veg] | 0.022 | N.D. | N.A. |
| 1A751 [pM2VegCenA] | 0.088 | 8.3 | 99.2 |

N.A. - Not applicable
N.D. - Not detectable

What is claimed is:

1. An endonuclease-protected vegI promoter.

2. An endonuclease-protected vegI promoter according to claim 1, wherein it is a *B. subtilis* endonuclease-protected vegI promoter.

3. The endonuclease-protected vegI promoter according to claim 1, having a modified restriction endonuclease site protected against endonuclease digestion, wherein the restriction site in unmodified form has the sequence of SEQ ID NO:20.

4. The endonuclease-protected vegI promoter according to claim 3, wherein the modified endonuclease restriction site has the sequence of SEQ ID NO: 21.

5. The endonuclease-protected vegI promoter according to claim 1 having a protected endonuclease restriction site at nucleotides −15 to −8 relative to the transcription start nucleotide beginning at +1, said start nucleotide corresponding to nucleotide 51 of SEQ ID NO: 12 or SEQ ID NO: 13.

6. An endonuclease-protected vegI promoter according to claim 5, having the sequence of SEQ ID NO: 12.

7. A vegI promoter having a guanine nucleotide substituted at position −11 relative to the transcription start nucleotide beginning at nucleotide +1, said start nucleotide corresponding to nucleotide 51 of SEQ ID NO: 12 or SEQ ID NO: 13.

8. A DNA construct for expressing a coding sequence in *B. subtilis,* comprising operatively linked in the 5' to 3' direction:
 a) an endonuclease-protected vegI promoter;
 b) a DNA coding sequence encoding an expression product; and
 c) a 3' non-translated region.

9. A DNA construct according to claim 8, additionally comprising between said endonuclease-protected vegI promoter and said DNA coding sequence a lac operator, ribosome binding site, and SPA leader sequence.

10. A DNA construct according to claim 8, said 3' non-translated region comprising a stop codon and the gnt transcriptional terminator.

11. A DNA construct according to claim 8, said DNA coding sequence comprising the coding sequence for a heterologous protein.

12. A DNA construct according to claim 11, said DNA coding sequence comprising the *Cellulomonas fimi* cenA coding sequence.

13. A DNA construct according to claim 11, said DNA coding sequence comprising the human epidermal growth factor coding sequence.

14. A bacterium transformed with a DNA construct according to any one of claims 11–13.

15. A bacterium according to claim 14, the bacterium being selected from the group consisting *B. subtilis* and *E. coli.*

16. A bacterium transformed with a DNA construct according to claim 8.

17. A bacterium according to claim 16, the bacterium being selected from the group consisting *B. subtilis* and *E. coli.*

18. A method for producing an expression product of a DNA coding sequence, comprising the steps of:
 a) transforming a bacterium with the DNA construct according to claim 7 containing said DNA coding sequence encoding said expression product;
 b) culturing said bacterium to cause expression of said coding sequence; and
 c) isolating and purifying said expression product.

19. A DNA construct for expressing a coding sequence in *B. subtilis,* comprising operatively linked in the 5' to 3' direction:
 a) an endonuclease-protected vegI promoter;
 b) at least one cloning site into which may be inserted a DNA coding sequence encoding an expression product; and
 c) a 3' non-translated region.

20. A DNA construct according to claim 9, said cloning site comprising a multiple cloning site.

21. A DNA construct according to claim 19, additionally comprising between said endonuclease-protected vegI promoter and said cloning site a lac operator, ribosome binding site, and SPA leader sequence.

22. A DNA construct according to claim 19, said 3' non-translated region comprising a stop codon and the gnt transcriptional terminator.

23. A bacterium transformed with a DNA construct according to claim 17.

24. A bacterium according to claim 23, the bacterium being selected from the group consisting *B. subtilis* and *E. coli.*

25. An *E. coli* bacterium transformed with a DNA construct for expressing a coding sequence, said DNA construct comprising operatively linked in the 5' to 3' direction:
 a) the vegI promoter;
 b) a DNA coding sequence encoding an expression product; and
 c) a 3' non-translated region.

26. A method for producing an expression product of a DNA coding sequence, comprising the steps of:
 a) culturing a transformed *E. coli* according to claim 25, said *E. coli* having been transformed with a DNA construct containing said DNA coding sequence encoding said expression product, wherein said culturing provides for expression of said coding sequence; and
 b) isolating and purifying said expression product.

* * * * *

UNITED STATES PATENT AND TRADEMARK OFFICE
CERTIFICATE OF CORRECTION

PATENT NO. : 6,146,848  Page 1 of 1
DATED : November 14, 2000
INVENTOR(S) : Wong et al.

It is certified that error appears in the above-identified patent and that said Letters Patent is hereby corrected as shown below:

Column 20,
Line 16, "claim 9," should read -- claim 19, --
Line 26, "claim 17," should read -- claim 19. --
Line 28, "consisting" should read -- consisting of --

Signed and Sealed this

Twenty-seventh Day of November, 2001

Attest:

*Nicholas P. Godici*

NICHOLAS P. GODICI
*Attesting Officer*  *Acting Director of the United States Patent and Trademark Office*

SEQUENCE LISTING

<160> NUMBER OF SEQ ID NOS: 21

<210> SEQ ID NO 1
<211> LENGTH: 70
<212> TYPE: DNA
<213> ORGANISM: Artificial Sequence
<220> FEATURE:
<223> OTHER INFORMATION: Description of Artificial Sequence:synthetic
      oligonucleotide encoding Veg cassette

<400> SEQUENCE: 1
gggggaattc taatttaaat tttatttgac aaaaatgggc tcgtgttgtg caataaatgt      60
agtgaggtgg                                                             70

<210> SEQ ID NO 2
<211> LENGTH: 67
<212> TYPE: DNA
<213> ORGANISM: Artificial Sequence
<220> FEATURE:
<223> OTHER INFORMATION: Description of Artificial Sequence:synthetic
      oligonucleotide encoding Veg cassette

<400> SEQUENCE: 2
ggaggtgata aaattgaaaa agaaaaacat ttattcaatt cgtaaactag gtgtaggtat      60
tgcatct                                                                67

<210> SEQ ID NO 3
<211> LENGTH: 67
<212> TYPE: DNA
<213> ORGANISM: Artificial Sequence
<220> FEATURE:
<223> OTHER INFORMATION: Description of Artificial Sequence:synthetic
      oligonucleotide encoding Veg cassette

<400> SEQUENCE: 3

-continued

```
ggtggcgtaa cacctgctgc aaatgctgcg caacacgatg aagctcaaca aaatgcttct    60
agacccg                                                               67

<210> SEQ ID NO 4
<211> LENGTH: 70
<212> TYPE: DNA
<213> ORGANISM: Artificial Sequence
<220> FEATURE:
<223> OTHER INFORMATION: Description of Artificial Sequence:synthetic
      oligonucleotide encoding Veg cassette

<400> SEQUENCE: 4
taaaaacacg gtcagtttca actgaaccgt gttttttttct tctatcccaa acaacagaag    60
ggtaccgggg                                                            70

<210> SEQ ID NO 5
<211> LENGTH: 68
<212> TYPE: DNA
<213> ORGANISM: Artificial Sequence
<220> FEATURE:
<223> OTHER INFORMATION: Description of Artificial Sequence:synthetic
      oligonucleotide encoding Veg cassette

<400> SEQUENCE: 5
ttttcaattt tatcacctcc tttgtgaaat tgttatccgc tcacaattcc acctcactac    60
atttattg                                                              68

<210> SEQ ID NO 6
<211> LENGTH: 67
<212> TYPE: DNA
<213> ORGANISM: Artificial Sequence
<220> FEATURE:
<223> OTHER INFORMATION: Description of Artificial Sequence:synthetic
      oligonucleotide encoding Veg cassette

<400> SEQUENCE: 6
gcagcaggtg ttacgccacc agatataagt aatgtaccta agttacaga tgcaatacct     60 acaccta                                                               67

<210> SEQ ID NO 7
<211> LENGTH: 67
<212> TYPE: DNA
<213> ORGANISM: Artificial Sequence
<220> FEATURE:
<223> OTHER INFORMATION: Description of Artificial Sequence:synthetic
      oligonucleotide encoding Veg cassette

<400> SEQUENCE: 7
tgaaactgac cgtgttttta atacaggtta cttaattaat taagccccgg gtctagaagc    60
attttgt                                                               67

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide encoding Veg cassette

<400> SEQUENCE: 8
ccccggtacc cttctgttgt                                                 20
```

```
<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence:PCR overlap
      extension primers

<400> SEQUENCE: 9
agcggataac aatttcacac agga                                              24

<210> SEQ ID NO 10
<211> LENGTH: 60
<212> TYPE: DNA
<213> ORGANISM: Artificial Sequence
<220> FEATURE:
<223> OTHER INFORMATION: Description of Artificial Sequence:PCR overlap
      extension primers

<400> SEQUENCE: 10
gtgggacagg ggacattcag agtcactatt agcatttgca gcaggtgtta cgccaccaga       60

<210> SEQ ID NO 11
<211> LENGTH: 30
<212> TYPE: DNA
<213> ORGANISM: Homo sapiens
<220> FEATURE:
<223> OTHER INFORMATION: Description of Artificial Sequence:PCR overlap
      extension primers

<400> SEQUENCE: 11
aatagtgact ctgaatgtcc cctgtcccac                                        30

<210> SEQ ID NO 12
<211> LENGTH: 60
<212> TYPE: DNA
<213> ORGANISM: Bacillus subtilis

<400> SEQUENCE: 12
taatttaaat tttatttgac aaaaatgggc tcgtgttgtg caataaatgt agtgaggtgg       60

<210> SEQ ID NO 13
<211> LENGTH: 60
<212> TYPE: DNA
<213> ORGANISM: Bacillus subtilis

<400> SEQUENCE: 13
taatttaaat tttatttgac aaaaatgggc tcgtgttgta caataaatgt agtgaggtgg       60

<210> SEQ ID NO 14
<211> LENGTH: 25
<212> TYPE: DNA
<213> ORGANISM: Escherichia coli

<400> SEQUENCE: 14
aattgtgagc ggataacaat ttcac                                             25

<210> SEQ ID NO 15
<211> LENGTH: 16
<212> TYPE: DNA
<213> ORGANISM: Bacillus subtilis

<400> SEQUENCE: 15
aaaggaggtg ataaaa                                                       16
```

```
-continued

<210> SEQ ID NO 16
<211> LENGTH: 138
<212> TYPE: DNA
<213> ORGANISM: Staphylococcus aureus

<400> SEQUENCE: 16
ttgaaaaaga aaacattta ttcaattcgt aaactaggtg taggtattgc atctgtaact        60
ttaggtacat tacttatatc tggtggcgta acacctgctg caaatgctgc gcaacacgat      120
gaagctcaac aaaatgct                                                   138

<210> SEQ ID NO 17
<211> LENGTH: 12
<212> TYPE: DNA
<213> ORGANISM: Artificial Sequence
<220> FEATURE:
<223> OTHER INFORMATION: Description of Artificial Sequence:Multiple
      cloning region

<400> SEQUENCE: 17
tctagacccg gg                                                          12

<210> SEQ ID NO 18
<211> LENGTH: 15
<212> TYPE: DNA
<213> ORGANISM: Artificial Sequence
<220> FEATURE:
<223> OTHER INFORMATION: Description of Artificial Sequence:stop codon

<400> SEQUENCE: 18
gcttaattaa ttaag                                                       15

<210> SEQ ID NO 19
<211> LENGTH: 70
<212> TYPE: DNA
<213> ORGANISM: Bacillus subtilis

<400> SEQUENCE: 19
taacctgtat taaaaacacg gtcagtttca actgaaccgt gttttttct tctatcccaa        60 acaacagaag                                                             70

<210> SEQ ID NO 20
<211> LENGTH: 8
<212> TYPE: DNA
<213> ORGANISM: Bacillus subtilis

<400> SEQUENCE: 20 ttgtacaa                                                                8

<210> SEQ ID NO 21
<211> LENGTH: 8
<212> TYPE: DNA
<213> ORGANISM: Bacillus subtilis

<400> SEQUENCE: 21 ttgtgcaa                                                                8
```